United States Patent
Magni et al.

[11] Patent Number: 6,043,368
[45] Date of Patent: *Mar. 28, 2000

[54] METHOD OF MAKING THIENO-PYRIDINE DERIVATIVES

[75] Inventors: Ambrogio Magni, Osnago; Giovanni Signorelli, Milan, both of Italy

[73] Assignee: Poli Industria Chimica, S.P.A., Milan, Italy

[*] Notice: This patent issued on a continued prosecution application filed under 37 CFR 1.53(d), and is subject to the twenty year patent term provisions of 35 U.S.C. 154(a)(2).

[21] Appl. No.: 08/707,658

[22] Filed: Sep. 4, 1996

[51] Int. Cl.[7] .............. C07D 495/04; C07D 333/14
[52] U.S. Cl. .............. 546/114; 549/59; 549/74; 549/75; 549/76; 549/77; 549/78
[58] Field of Search ............... 546/114; 549/74, 549/75, 76, 78, 59, 77

[56] References Cited

U.S. PATENT DOCUMENTS

| | | | |
|---|---|---|---|
| 4,051,141 | 9/1977 | Castaigne | 260/294.8 |
| 4,080,447 | 3/1978 | Amselem | 424/232 |
| 4,127,580 | 11/1978 | Braye | 546/114 |
| 4,174,448 | 11/1979 | Bousquet et al. | 546/114 |
| 4,490,377 | 12/1984 | Chowhan | 424/256 |
| 4,591,592 | 5/1986 | Chowhan | 514/301 |
| 4,730,049 | 3/1988 | Suguro | 546/114 |
| 4,873,343 | 10/1989 | Radisson | 549/74 |
| 4,874,876 | 10/1989 | O'Reilly et al. | 549/49 |
| 4,906,756 | 3/1990 | Lodewijk et al. | 546/114 |
| 4,963,559 | 10/1990 | Suzuki | 514/301 |
| 4,965,359 | 10/1990 | Gosteli et al. | 546/114 |
| 4,990,618 | 2/1991 | Gosteli et al. | 546/221 |
| 4,997,945 | 3/1991 | Khatri | 546/114 |
| 5,068,360 | 11/1991 | DeHoff | 549/74 |
| 5,132,435 | 7/1992 | Bousquet et al. | 549/60 |
| 5,191,090 | 3/1993 | DeHoff | 549/74 |
| 5,296,603 | 3/1994 | Yamakawa et al. | 546/114 |
| 5,382,577 | 1/1995 | Odawara et al. | 514/211 |
| 5,520,928 | 5/1996 | Sherman | 424/464 |

FOREIGN PATENT DOCUMENTS

| | | |
|---|---|---|
| 2100836 | 1/1995 | Canada. |
| 0313472 A1 | 10/1988 | European Pat. Off.. |
| 0377413 A1 | 1/1989 | European Pat. Off.. |
| 0439404 A2 | 1/1991 | European Pat. Off.. |
| 0522956 A2 | 7/1992 | European Pat. Off.. |
| 0573975 A1 | 6/1993 | European Pat. Off.. |
| 2614619 | 11/1988 | France. |
| 62205087 | 9/1987 | Japan. |
| 3157382 | 7/1991 | Japan. |
| 4-26690 | 1/1992 | Japan. |
| 6271582 | 9/1994 | Japan. |

OTHER PUBLICATIONS

Sumita et al.; "A Modified Mannich Reaction Using 1,3–Dioxolane;" Chem. Pharm. Bull. 42(8), vol. 42, No. 8, pp. 1676–1678. 1994.

*Primary Examiner*—Evelyn Mei Huang
*Attorney, Agent, or Firm*—Townsend and Townsend and Crew LLP

[57] ABSTRACT

The present invention provides a method of preparing thieno [3,2-c]pyridine derivatives of formula I:

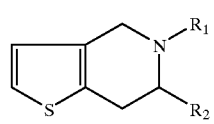

I wherein $R_1$ is selected from the group consisting of lower alkyl; lower alkylene phenyl; substituted lower alkylene phenyl wherein the phenyl is substituted from 1 to 3 times with lower alkyl, lower alkoxy, lower acyloxy, hydroxy, nitro and halo; lower alkylene naphthyl, lower alkylene thienyl; lower alkylene diphenyl; lower alkylene-hydroxy-phenyl; substituted lower alkylene-hydroxy-phenyl wherein the phenyl is substituted from 1 to 3 times with lower alkyl, lower alkoxy, lower acyloxy, hydroxy, nitro, and halo; lower alkylene-hydroxy-naphthyl; lower alkylene-hydroxy-thienyl; lower alkylene-hydroxy-diphenyl, and $R_2$ is H or lower alkylene. The method comprises reacting a compound of a formula II:

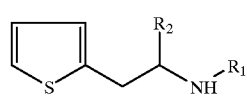

II with a cyclic dioxy or cyclic dithio in the presence of catalyst.

17 Claims, No Drawings

METHOD OF MAKING THIENO-PYRIDINE DERIVATIVES

FIELD OF THE INVENTION

The present invention relates to methods for synthesizing thieno[3,2-c]pyridine derivatives, particularly 5-[(2-chlorophenyl)methyl]-4,5,6,7-tetrahydrothieno[3,2-c] pyridine and salts thereof, (i.e., ticlopidine hydrochloride). More specifically, the present invention relates to a more direct method of preparing thieno[3,2-c]pyridine derivatives.

BACKGROUND OF THE INVENTION

Thieno[3,2-c]pyridine derivatives, and particularly ticlopidine hydrochloride are known for their anti-inflammatory activity, vaso dilating activity, and blood platlet aggregation inhibitor activity, as described in U.S. Pat. No. 4,051,141 to Castaigne, the disclosure of which is incorporated herein by reference in its entirety.

Several methods are known for the synthesis of thieno[3, 2-c]pyridine derivatives. For Example, U.S. Pat. No. 4,051, 141 to Castaigne, proposed the synthesis of thieno-pyridine derivatives by condensation of a thieno[3,2-c]pyridine with o-chlorobenzyl chloride. U.S. Pat. No. 4,127,580 to Braye proposed another method of synthesizing thieno-pyridine derivatives. According to the method of Braye '580, ticlopidine could be prepared by reacting N-(2-chloro-benzyl)-2-(2- thienyl)ethylamine hydrochloride with formaldehyde to achieve the conversion to a free base, which could then be converted to the hydrochloride salt. U.S. Pat. No. 4,174,448 to Bousquet et al. proposes the reaction of N-(2-chloro-benzyl)-2-(2-thienyl)ethylamine hydrochloride with a halogenomethyl ether, a halogenomethyl thio ether, a halogenomethyl ester, a S-hexahydro-S-triazine, a trioxane, dimethoxymethane, or a trithian to yield thieno-pyridine derivatives.

Still other proposed synthetic pathways utilize 2-(2-thienyl)ethylamine as the key intermediate to produce thieno-pyridine derivatives. For example, Japanese Patent No. 4-26690 proposes a method of preparing ticlopidine by reacting 2-(2-thienyl)ethylamine with 1,3-dioxolane.

U.S. Pat. No. 4,906,756 to Lodewijk et al. proposes the reaction of 2-(2-thienyl)ethylamine, prepared from 2-(2-nitrovinyl)thiophene, with formaldehyde to produce the formimine, cyclizing the formimine with hydrochloric acid to produce 4,5,6,7-tetrahydrothieno[3,2,c]pyridine, and converting this compound to ticlopidine free base by reaction with o-chlorobenzylchloride. The free base is then converted to ticlopidine hydrochloride.

U.S. Pat. No. 4,997,945 to Khatri proposes a method of making ticlopidine which involves reacting 2-(2'-thienyl) ethylamine, prepared from the carbamate salt thereof, with formaldehyde and proceeded as described in Lodewijk '756.

U.S. Pat. Nos. 5,068,360 and 5,191,090 both to DeHoff propose reacting an alkyl thienyl with gaseous or liquid ammonia respectively to produce 2-(2'-thienyl)ethylamine, and then producing ticlopidine by reaction of this intermediate with formaldehyde as described in Braye '580 and Lodewijk '756.

Accordingly, there remains a need in the art for additional methods of preparing thieno[3,2-c]pyridine derivatives such as ticlopidine hydrochloride. In addition, there remains a need in the art for methods of synthesizing thieno[3,2-c] pyridine derivatives which produce commercially viable yields of product in a relatively simple manner. Further, there remains a need in the art for a method of preparing thieno[3,2-c]pyridine derivatives which avoids the use of formaldehyde utilized in conventional manufacturing methods.

It is therefore an object of the present invention to provide a new method of preparing thieno[3,2-c]pyridine derivatives such as ticlopidine hydrochloride. It is further an object of the present invention to provide a method of preparing thieno[3,2-c]pyridine derivatives which avoids the use of formaldehyde.

SUMMARY OF THE INVENTION

As a first aspect, the present invention provides a method of preparing thieno[3,2-c]pyridine derivatives of formula I:

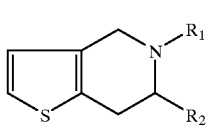

I wherein $R_1$ is selected from the group consisting of lower alkyl; lower alkylene phenyl; substituted alkylene phenyl wherein the phenyl is substituted between 1 and 3 times with lower alkyl, lower alkoxy, lower acyloxy, hydroxy, nitro and halo; lower alkylene naphthyl, lower alkylene thienyl; lower alkylene diphenyl; lower alkylene-hydroxy-phenyl; substituted lower alkylene-hydroxy-phenyl wherein the phenyl is substituted between 1 and 3 times with lower alkyl, lower alkoxy, lower acyloxy, hydroxy, nitro, and halo; lower alkylene-hydroxy-naphthyl; lower alkylene-hydroxy-thienyl; lower alkylene-hydroxy-diphenyl, and $R_2$ is H or lower alkyl, and pharmaceutically acceptable salts thereof.

The method comprises comprising reacting a compound of a formula II:

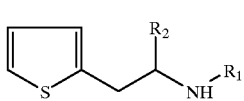

II with a cyclic dioxy or a cyclic dithio in the presence of catalyst (e.g., hydrochloric acid).

As a second aspect, the present invention provides a method of preparing thieno[3,2-c]pyridine derivatives of formula I and pharmacuetically acceptable salts thereof comprising the steps of: a) reacting a thienyl of formula III:

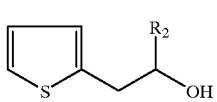

III wherein $R_2$ is H or lower alkyl, with a sulfonyl halide of formula IV:

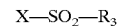

$$X\text{—}SO_2\text{—}R_3 \qquad \text{IV}$$

wherein X is a halo, and $R_3$ is selected from the group consisting of methyl trichloromethyl, trifluoromethyl, phenyl, p-methyl phenyl, m-acetyl phenyl, and p-bromophenyl to produce a sulphonate intermediate; b) reacting the sulphonate intermediate with an amine of formula V:

to produce a compound of formula II, and c) reacting the compound of formula II with a cyclic dioxy or a cyclic dithio in the presence of catalyst, to produce the thieno[3,2-c] pyridine derivatives.

In one preferred embodiment, the present invention provides a method of preparing ticlopidine hydrochloride by reacting N-[(2-chlorophenyl-methyl)]-2-(2-thienyl) ethylamine hydrochloride with a cyclic dioxy or a cyclic dithio in the presence of a catalyst.

The foregoing and other objects and aspects of the present invention are explained in detail in the detailed description and examples set forth below.

DETAILED DESCRIPTION OF THE INVENTION

As used herein, the term "lower alkyl" or "lower alkylene" refers to a $C_1$–$C_8$ linear, branched, or cyclic, saturated or unsaturated alkyl or alkylene, such as methyl, ethyl, propyl, isopropyl, butyl, isobutyl, t-butyl, pentyl, hexyl, octyl, and the like. The term "lower alkoxy" similarly refers to a $C_1$–$C_8$ linear or branched alkoxy, such as methoxy, ethoxy, propoxy, isopropoxy, butoxy, and the like. The term "halo" or "halogen" refers to any halogen including fluorine, chlorine, bromine, and iodine.

According to the methods of the present invention, thieno[3,2-c]pyridine derivatives of formula I:

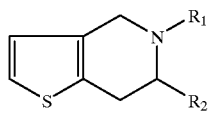

wherein $R_1$ is selected from the group consisting of lower alkyl; lower alkylene phenyl; substituted lower alkylene phenyl wherein the phenyl is substituted between 1 and 3 times with lower alkyl, lower alkoxy, lower acyloxy, hydroxy, nitro and halo; lower alkylene naphthyl, lower alkylene thienyl; lower alkylene diphenyl; lower alkylene-hydroxy-phenyl; substituted lower alkylene-hydroxy-phenyl wherein the phenyl is substituted between 1 and 3 times with lower alkyl, lower alkoxy, lower acyloxy, hydroxy, nitro, and halo; lower alkylene-hydroxy-naphthyl; lower alkylene-hydroxy-thienyl; lower alkylene-hydroxy- diphenyl, and $R_2$ is H or lower alkyl, and pharmaceutically acceptable salts thereof;

are prepared according to the following reaction Scheme 1.

Scheme 1

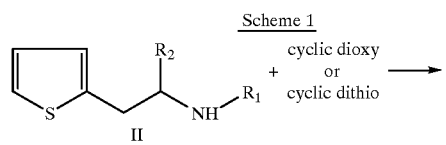

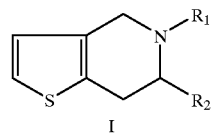

Specific examples of preferred thieno[3,2-c]pyridine derivatives which may be produced according to the methods of the present invention include but are not limited to compounds of formula I wherein $R_1$ is selected from the group consisting of methylene phenyl; alkyl substituted methylene phenyl, such as mono-methyl substituted methylene phenyl or di-methyl substituted methylene phenyl; halo substituted methylene phenyl, such as mono-fluoro substituted methylene phenyl, mono-chloro substituted methylene phenyl, or di-chloro substituted methylene phenyl; hydroxy substituted methylene phenyl; acetoxy substituted methylene phenyl; alkoxy substituted methylene phenyl, such as methoxy substituted methylene phenyl, dimethoxy substituted methylene phenyl, or trimethoxy substituted methylene phenyl; nitro substituted methylene phenyl; ethylene phenyl; methylene naphthyl; methylene thienyl halide; ethylene hydroxy phenyl; propylene hydroxy phenyl; halo substituted ethylene hydroxy phenyl; hydroxy substituted ethylene hydroxy phenyl; methoxy substituted ethylene hydroxy phenyl; dimethoxy substituted ethylene hydroxy phenyl; and ethylene hydroxy thienyl.

Specific examples of pharmaceutically acceptable salts of the compounds of formula I include but are not limited to hydrofluoride, hydrochloride, hydrobromide, hydroiodide, methiodide, maleate, methylsulphonate, and fumarate salts of the compound of formula I.

The compounds of the formula I and salts thereof are prepared by reacting the compounds of formula II with a cyclic dioxy or a cyclic dithio in the presence of a catalyst. The compounds of formula II:

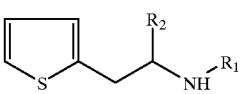

wherein $R_1$ is selected from the group consisting of lower alkyl; lower alkylene phenyl; substituted lower alkylene phenyl wherein the phenyl is substituted between 1 and 3 times with lower alkyl, lower alkoxy, lower acyloxy, hydroxy, nitro and halo; lower alkylene naphthyl, lower alkylene thienyl; lower alkylene diphenyl; lower alkylene-hydroxy-phenyl; substituted lower alkylene-hydroxy-phenyl wherein the phenyl is substituted between 1 and 3 times with lower alkyl, lower alkoxy, lower acyloxy, hydroxy, nitro, and halo; lower alkylene-hydroxy-naphthyl; lower alkylene-hydroxy-thienyl; lower alkylene-hydroxy-diphenyl, and $R_2$ is H or lower alkylene; are known in the art and can be prepared according to conventional methods known in the art. For example the compounds of formula II and methods of their preparation are described in U.S. Pat. No. 4,127,580 to Braye, the disclosure of which is incorporated herein by reference in its entirety.

Specific examples of compounds of formula II which may be employed in the methods of the present invention include but are not limited to compounds of formula II wherein $R_1$ is selected from the group consisting of methylene phenyl; alkyl substituted methylene phenyl, such as mono-methyl substituted methylene phenyl or di-methyl substituted methylene phenyl; halo substituted methylene phenyl, such as mono-fluoro substituted methylene phenyl, mono-chloro substituted methylene phenyl, or di-chloro substituted methylene phenyl; hydroxy substituted methylene phenyl; acetoxy substituted methylene phenyl; alkoxy substituted methylene phenyl, such as methoxy substituted methylene phenyl, dimethoxy substituted methylene phenyl, or trimethoxy substituted methylene phenyl; nitro substituted methylene phenyl; ethylene phenyl; methylene naphthyl; methylene thienyl halide; ethylene hydroxy phenyl; propylene hydroxy phenyl; halo substituted ethylene hydroxy phenyl; hydroxy substituted ethylene hydroxy phenyl; methoxy substituted ethylene hydroxy phenyl; dimethoxy substituted ethylene hydroxy phenyl; and ethylene hydroxy thienyl. The currently preferred compounds of formula II are those compounds wherein $R_1$ is substituted alkylene phenyl wherein the phenyl is substituted between 1 and 3 times with lower alkyl, lower alkoxy, lower acyloxy, hydroxy, nitro, or halo, and $R_2$ is lower alkyl. In one particularly preferred embodiment, the compound of formula II is N-[(2-chlorophenyl-methyl)]-2-(2-thienyl)ethylamine hydrochloride (i.e., $R_1$ is chloro-substituted alkylene phenyl, and $R_2$ is methyl).

The preferred method of preparing the compounds of Formula II proceeds according to the following Scheme 2.

Scheme 2

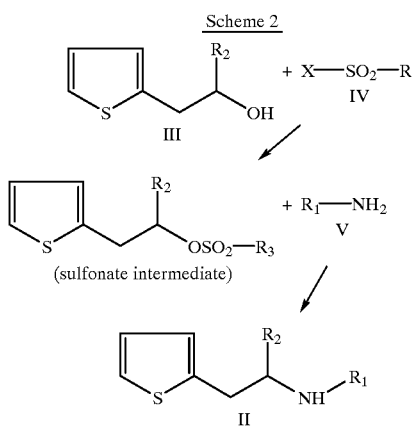

In the thienyls of formula III utilized in Scheme 1:

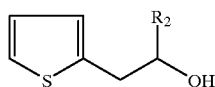

$R_2$ is as defined above and such thienyls, are known in the art. Specific examples of thienyls of formula III which are useful in the methods of the present invention include but are not limited to 2-(2-thienyl)ethanol, 2-(2-thienyl)ethanol methane, 2-(2-thienyl)ethanol ethane, 2-(2-thienyl)ethanol propane, 2-(2-thienyl)ethanol isopropane, 2-(2-thienyl) ethanol butane, 2-(2-thienyl)ethanol pentane, and the like.

The thienyls of formula III are reacted with a sulfonyl halide of formula IV:

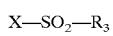 IV wherein X is a halo, and $R_3$ is selected from the group consisting of methyl, trichloromethyl, trifluoromethyl, phenyl, p-methyl phenyl, m-acetyl phenyl, and p-bromophenyl. Preferred sulfonyl halides include but are not limited to methane sulfonyl chloride, trichloromethane sulfonyl chloride, trifluoromethane sulfonyl chloride, benzene sulfonyl chloride, para-toluene sulfonyl chlroide, m-acetyl benzene sulfonyl fluoride, p-bromophenyl sulfonyl chloride, and the like.

The reaction is typically carried out under basic conditions, such as in the presence of compounds selected from the group consisting of tertiary amines such as trialkylamine or triaryldialkylamines; pyridines; quinolines; and acid derivatives such as alkali metal carbonates, alkali metal hydrides, alkali earth metal hydrides, and metal alkoxides. The reaction is preferably conducted under atmospheric pressure at a temperature of between about 5 and about 50° C., although other suitable reaction conditions will be known to those skilled in the art.

The reaction produces the sulphonate intermediate which is then reacted with an amine of formula V:

$$R_1-NH_2 \quad\quad V$$

wherein $R_1$ is as defined hereinabove. Preferred amines include but are not limited to 2-chlorobenzylamine, 2,6-dichlorobenzylamine, 2-fluorobenzylamine, 2-methoxybenzylamine, and 2-nitrobenzylamine.

The reaction is typically carried out in an organic solvent. Suitable solvents will be well known to those skilled in the art and include, for example, toluene. The reaction is preferably conducted under atmospheric pressure at the reflux temperature of the organic solvent chosen, although other suitable reaction conditions will be known to those skilled in the art. The reaction yields the key intermediate compound of formula II above.

According to the new methods of the present invention, the compounds of formula II above may then be converted directly to thieno[3,2-c]pyridine derivatives and pharmaceutically acceptable salts thereof by reaction with a compound selected from the group consisting of cyclic dioxys and cyclic dithios in the presence of a catalyst. Suitable cyclic dioxys include but are not limited to 1,3-dioxolane, 4-methyl-1,3-dioxane, 1,3-dioxane, and 1,4-dioxane. Suitable cyclic dithios include but are not limited to 4-methyl-1,3-dithiane, 1,3-dithiane, 1,4-dithiane, and 1,3-dithiolane.

The reaction is catalysed by the presence of an organic or inorganic acid catalyst. Suitable acid catalysts include but are not limited to hydrochloric acid, hydrobromic acid, hydrofluoric acid, hydroiodic acid, sulfuric acid, nitric acid, methanesulfonic acid, benzenesulfonic acid, p-toluenesulfonic acid, acetic acid, and the like. The amount of catalyst required to catalyze the reaction of the compound of formula II with the cyclic dioxy or cyclic dithio will depend upon the particular acid selected, but will be readily determinable by those skilled in the art. Advantageously, the amount of acid catalyst typically required to catalyze the reaction is only about 1 percent by weight of the reaction mixture. The preferred acid catalyst is hydrochloric acid because it is readily available and inexpensive.

The reaction is typically carried out at atmospheric pressure, and the temperature may range from about 40° C. to 120° C. or up to the reflux temperature of the cyclic dioxy, cyclic dithio, or inert reaction solvent. Preferably, the reaction is carried out from about 60° to 100° C., most preferably, at about 80° C.

The reaction may be carried out in the absence of a reaction solvent. In this embodiment, the cyclic dioxy or cyclic dithio functions as the reaction solvent. Alternatively, an inert reaction solvent may be used. Suitable reaction solvents for use in the methods of the present invention include but are not limited to methanol, ethanol, isopropanol, dioxane, ethylene glycol, acetonitrile, and the like. Other appropriate inert reaction solvents will be readily determinable by those skilled in the art and are contemplated by the instant invention.

In the embodiment wherein no additional reaction solvent aside from the cyclic dioxy or cyclic dithio is utilized, the cyclic dioxy or cyclic dithio is preferably provided in a molar excess with respect to the compound of formula II.

In the embodiment wherein an inert reaction solvent is employed, the cyclic dioxy or cyclic dithio can be provided in molar excess with respect to the compound of formula II, or in a stoichiometric amount in relation to the compounds of formula II. Preferably, according to this embodiment, the cyclic dioxy or cyclic dithio is provided in slight molar excess with respect to the compound of formula II.

The process of the present invention provides the distinct advantage that the thieno[3,2-c]pyridine derivative or the pharmaceutically acceptable salt thereof is directly obtained in quantitative yields with a high degree of purity. Additional purification techniques, although not required, may be carried out on the products of the present invention if desired. Suitable purification techniques are well known to those skilled in the art.

The methods of the present invention provide the further advantage that the synthesis may be carried out in a single reaction vessel in only one reaction step. As a further advantage, the methods of the present invention avoid the use of formaldehyde.

The following examples are provided to illustrate the present invention, and should not be construed as limiting thereof. In these examples, "g" means grams, "ml" means milliliters, "l" means liters, "° C." means degrees Centigrade, "HCl" means hydrochloride,

EXAMPLE 1

Preparation of Ticlopidine Hydrochloride

N-[(2-chlorophenyl-methyl)]-2-(2-thienyl)ethylamine HCl (28.8 g) is suspended in 75 ml of 1,3-dioxolane. Hydrochloric acid at 37% concentration (0.25 ml) is added and the temperature of the reaction mixture is brought to 80° C. for 5 hours. Thereafter the reaction is complete. The mixture is cooled to room temperature, and the compound precipitates out. To complete the precipitation and simplify filtration, 75 ml of ethyl acetate is added to the reaction mixture. The filter cake is washed with ethyl acetate (2×20 ml) and dried at 60° C. UV. Ticlopidine HCl (28.5 g, 95% yield) is obtained with m.p. 208–210° C.

$^1$H NMR (CDCl$_3$, 500 MHz) δ: 4.6 (s, 2H); 6.67 (d, 1H); 7.15 (d, 1H) 7.32–7.41 (m, 4H)

EXAMPLE 2

Preparation of Ticlopidine Hydrochloride

N-[(2-chlorophenyl-methyl)]-2-(2-thienyl)ethylamine HCl (28.8 g) is suspended in 75 ml of iso-propanol. 1,3-Dioxane (13.2 g) and 0.25 ml of hydrochloric acid (37% concentration) are added. The reaction mixture is heated to 80° C. for 24 hours. Thereafter, the mixture is cooled to 10° C. and the precipitate is filtered and washed twice with 10 ml of frozen iso-propanol. The product is desiccated at 60° C. UV to yield 24.6 g (82%) Ticlopidine hydrochloride with chemical-physical characteristics as described in Example 1.

EXAMPLE 3

Preparation of Intermediate

2-Chlorobenzylamine (28.3 g, 0.2 moles) in 100 ml of toluene is brought to reflux. A solution of 2-(2-thienyl)ethyl methane sulfonate (20.6 g, 0.1 moles) in 100 ml toluene is added dropwise over the course of 12–14 hours. The mixture is maintained at reflux for an additional 6 hours. Thereafter the mixture is cooled to 80° C., 200 ml of water is added, and the mixture is cooled to room temperature. The organic phase is separated and acidified with 3 N hydrochloric acid. The resulting hydrochloride is collected by filtration and washed with acetone to yield, after drying, 23.6 g (82%) of (N-[(2-chlorophenyl-methyl)]-2-(2-thienyl)ethylamine HCl) having a melting point of 149–151 ° C.

EXAMPLE 4

Preparation of Ticlopidine Hydrochloride

N-[(2-chlorophenyl-methyl)]-2-(2-thienyl)ethylamine HCl (14.4 g) is suspended into 50 ml of dimethoxyethane. 1,3-Dithiane (9 g) and 0.12 ml of 37% hydrochloride acid are added. The reaction mixture is refluxed for 24 hours. Thereafter, the mixture is cooled to 10° C. and the crystalline precipitate is filtered and washed twice with 5 ml of dimethoxyethane. The product is dried at 60° C. under vacuum to yield 9.4 g (62.7%) of ticlopidine hydrochloride having the same physico-chemical characteristics as reported in Example 1.

EXAMPLE 5

Preparation of 5-(2-methylbenzyl)-4,5,6,7-tetrahydro-thieno[3,2-c]pyridine HCl

N-[(2-methylbenzyl)]-2-(2-thienyl)ethylamine HCl (26.8 g, 0.1 moles) is suspended in 75 ml of 1,3-dioxolane. 0.25 ml of 37% hydrochloride acid is added. The reaction mixture is refluxed for 24 hours. Thereafter, the mixture is cooled to 10° C. and the crystalline precipitate is filtered and washed twice with 5 ml of isopropanol. The product is dried at 60° C. under vacuum to yield 17.4 g (62.7%) of 5-(2-methylbenzyl)-4,5,6,7-tetrahydro-thieno[3,2-c]pyridine HCl having a m.p. of 207–210° C.

EXAMPLE 6

Preparation of 5-(2-chlorobenzyl)-6-methyl-4,5,6,7-tetrahydro-thieno[3,2-c]pyridine HCl Preparation of N-2-chlorobenzyl-1-methyl-2-(2-thienyl) ethylamine:

To a solution of 1-(2-thienyl)-2-propanol (14.4 g) and triethylamine (10.5 g) in 60 ml of toluene, a solution of p-toluensulfonylchloride (19.0 g) into 40 ml of toluene is added dropwise. The mixture is stirred for 24 hours. The precipitate of triethylamine HCl is removed by filtration and the filtrate is added dropwise to a solution of 2-chlorobenzylamine (28.3 g, 0.2 moles) into 100 ml of toluene at the reflux temperature over the course of 12–14 hours. The heating is continued for an additional 6 hours. Thereafter the mixture is cooled to 80° C., 200 ml of water is added, and the mixture is further cooled to room temperature. The organic phase is separated and acidified with 3 M hydrochloric acid. The resulting hydrochloride is collected by filtration and washed with acetone to yield, after drying, 16.4 g (61.7%) of N-2-chlorobenzyl-1-methyl-2-(2-thienyl)ethylamine HCl having a m.p. 164–165° C.

Preparation of 5-(2-chlorobenzyl)-6-methyl-4,5,6,7-tetrahydro-thieno[3,2-c]pyridine HCl:

N-2-chlorobenzyl-1-methyl-2-(2-thienyl)ethylamine HCl (16.4 g) is suspended in 50 ml of 1,3-dioxolane. Hydrochloric acid (37% concentration) (0.2 ml) is added and the temperature of the reaction mixture is brought to 80° C. for 6 hours. When the reaction is complete, the mixture is cooled to room temperature, and the precipitation of the product is completed by adding 50 ml of ethyl acetate. The crystalline product is filtered, washed with ethyl acetate and dried under vacuum at 60° C. 5-(2-chlorobenzyl)-6-methyl-4,5,6,7-tetrahydro-thieno[3,2-c] pyridine HCl (10.7 g, 63% yield) is obtained having a m.p. 179–180° C.

EXAMPLE 7

Preparation of 5-(2,6-dichlorobenzyl)-6-methyl-4,5,6,7-tetrahydro-thieno[3,2-c]pyridine HCl N-(2,6-dichlorobenzyl)-2-(2-thienyl)ethylamine HCl (16.1 g, 0.05 moles) is suspended in 5 ml of 1,3-dioxolane and 50 ml of ethanol. Hydrochloric acid (37% concentration) (0.15 ml) is added. The reaction mixture is refluxed for 48 hours. Thereafter, the mixture is cooled to 10° C. and the crystalline precipitate is filtered and washed twice with 5 ml of ethanol. The product is dried at 60° C. under vacuum to yield 9.7 g (58.1%) of 5-(2,6-dichlorobenzyl)-6-methyl-4,5,6,7-tetrahydro-thieno[3,2-c] pyridine HCl having a m.p. 198–200° C.

EXAMPLE 8

Preparation of 5-(2-fluorobenzyl)-6-methyl-4,5,6,7-tetrahydro-thieno[3,2-c]pyridine maleate 5-(2-fluorobenzyl)-6-methyl-4,5,6,7-tetrahydro-thieno[3,2-c]pyridine maleate is prepared using the method described in Example 7. The product exhibits a m.p. 197–198° C.

EXAMPLE 9

Preparation of 5-(2-nitrobenzyl)-6-methyl-4,5,6,7-tetrahydro-thieno[3,2-c]pyridine HCl 5-(2-nitrobenzyl)-6-methyl-4,5,6,7-tetrahydro-thieno[3,2-c]pyridine HCl is prepared using the method described in Example 7. The product exhibits a m.p. 178–190° C.

EXAMPLE 10

Preparation of 5-(3-methoxybenzyl)-6-methyl-4,5,6,7-tetrahydro-thieno[3,2-c]pyridine HCl 5-(3-methoxybenzyl)-6-methyl-4,5,6, 7-tetrahydro-thieno [3, 2-c]pyridine HCl is prepared using the method described in Example 7. The product exhibits a m.p. 197–198° C.

The foregoing is illustrative of the present invention and is not to be construed as limiting thereof. The invention is defined by the following claims, with equivalents of the claims to be included therein.

That which is claimed is:

1. A process for preparing thieno[3,2-c]pyridine derivatives of formula I:

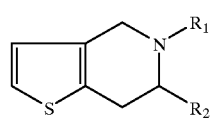

wherein:

$R_1$, is selected from the group consisting of lower alkyl; lower alkylene phenyl; substituted lower alkylene phenyl wherein the phenyl is substituted from 1 to 3 times with lower alkyl, lower alkoxy, lower acyloxy, hydroxy, nitro and halo; lower alkylene naphthyl, lower alkylene thienyl; lower alkylene diphenyl; lower alkylene-hydroxy-phenyl; substituted lower alkylene-hydroxy-phenyl wherein the phenyl is substituted from 1 to 3 times with lower alkyl, lower alkoxy, lower acyloxy, hydroxy, nitro, and halo; lower alkylene-hydroxy-naphthyl; lower alkylene-hydroxythienyl; lower alkylene-hydroxy-diphenyl, and $R_2$ is H or lower alkyl, or a pharmaceutically acceptable salt thereof;

said process comprising:

(a) reacting a compound of a formula II:

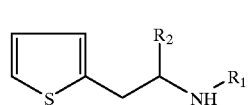

with a cyclic dioxy or a cyclic dithio in the presence of catalyst at an elevated temperature, thereby forming a reaction mixture; and (b) inducing said thieno[3,2-c]pyridine derivatives to crystallize directly from said reaction mixture, said thieno[3,2-c]pyridine derivatives being produced in 82% yield or greater when cyclic dioxy is employed.

2. The process according to claim 1, wherein the catalyst is selected from inorganic acids and organic acids.

3. The process according to claim 1, wherein the catalyst is selected from the group consisting of hydrochloric acid, hydrobromic acid, methanesulfonic acid, benzenosulfonic acid, p-toluenesulfonic acid.

4. The process according to claim 1, wherein $R_1$ is a substituted alkylene phenyl wherein phenyl is substituted between 1 and 3 times with lower alkyl, lower alkoxy, lower acyloxy, hydroxy, nitro and halo.

5. The process according to claim 1, wherein $R_1$ is substituted alkylene phenyl wherein phenyl is substituted between 1 and 3 times with halo.

6. The process according to claim 1 wherein the catalyst is hydrochloric acid.

7. The process according to claim 1 wherein the process is carried out at atmospheric pressure and a temperature of from about 40° C. to 120° C.

8. The process according to claim 1 wherein the process is carried out at a temperature of about 80° C.

9. The process according to claim 1, wherein the process is carried out at a reflux temperature of the cyclic dioxy or the cyclic dithio.

10. The process according to claim 1 wherein the process is carried out in an organic solvent.

11. The process according to claim 1, wherein the organic solvent is selected from the group consisting of methanol, ethanol, isopropanol, dioxane, ethylene glycol, dimethoxyethane, and acetonitrile.

12. A process for preparing thienyl pyridine derivatives of formula I:

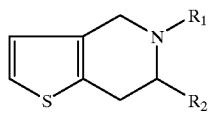

I wherein:

R$_1$ is selected from the group consisting of lower alkyl; lower alkylene phenyl; substituted lower alkylene phenyl wherein the phenyl is substituted from 1 to 3 times with lower alkyl, lower alkoxy, lower acyloxy, hydroxy, nitro and halo; lower alkylene naphthyl, lower alkylene thienyl; lower alkylene diphenyl; lower alkylene-hydroxy-phenyl; substituted lower alkylene-hydroxyphenyl wherein the phenyl is substituted from 1 to 3 times with lower alkyl, lower alkoxy, lower acyloxy, hydroxy, nitro, and halo; lower alkylene-hydroxy-naphthyl; lower alkylene-hydroxythienyl; lower alkylene-hydroxy-diphenyl; and R$_2$ is H or lower alkyl, or a pharmaceutically acceptable salt thereof;

said process comprising:

a) reacting a thienyl of formula III:

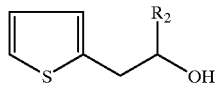

III with a sulfonyl halide of formula IV:

IV wherein X is a halo, and

R$_3$ is selected from the group consisting of methyl, trichloromethyl, trifluoromethyl, phenyl, p-methyl phenyl, m-acetyl phenyl, and p-bromophenyl, to produce a sulfonate intermediate;

b) reacting said sulfonate intermediate with an amine of formula V:

V to produce a compound of Formula II:

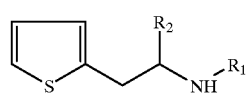

II c) reacting the compound of formula II with a cyclic dioxy or a cyclic dithio in the presence of catalyst at an elevated temperature, thereby forming a reaction mixture; and d) inducing said thieno pyridine derivatives to crystallize directly from said reaction mixture, said thieno pyridine derivative being produced in 82% yield or greater when cyclic dioxy is employed.

13. A process of producing ticlopidine hydrochloride, said process comprising:

(a) reacting N-2-(2-thienyl)ethylamine hydrochloride with a cyclic dioxy or a cyclic dithio in the presence of a catalyst at an elevated temperature, thereby forming a reaction mixture; and b) inducing said ticlopidine hydrochloride to crystallize directly from said reaction mixture, said ticlopidine hydrochloride being produced in 82% yield or greater when cyclic dioxy is employed.

14. The process according to claim 13, wherein said cyclic dioxy is 1,3-dioxolane and said catalyst is hydrochloric acid.

15. The process according to claim 13, wherein said cyclic dioxy is 1,3-dioxane and said catalyst is hydrochloric acid.

16. The process according to claim 13, wherein said cyclic dithio is 1,3-dithiane and said catalyst is hydrochloric acid.

17. The process according to claim 15, wherein said cyclic dithio is 1,3-dithiolane and said catalyst is hydrochloric acid.

* * * * *

UNITED STATES PATENT AND TRADEMARK OFFICE
CERTIFICATE OF CORRECTION

PATENT NO. : 6,043,368
DATED : March 28, 2000
INVENTOR(S) : Ambrogio Magni, *et al.*

It is certified that error appears in the above-identified patent and that said Letters Patent is hereby corrected as shown below:

Column 11, claim 11, line 6, please delete "1" and insert therefor --10--.

Signed and Sealed this

Twentieth Day of June, 2000

Attest:

Q. TODD DICKINSON

*Attesting Officer*  *Director of Patents and Trademarks*